US00PP15041P2

(12) United States Plant Patent
Olesen et al.

(10) Patent No.: US PP15,041 P2
(45) Date of Patent: Jul. 27, 2004

(54) MINIATURE ROSE PLANT NAMED 'POULHI018'

(50) Latin Name: *Rosa hybrida*
Varietal Denomination: POULhi018

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/686,286

(22) Filed: Oct. 14, 2003

(51) Int. Cl.[7] ..... A01H 5/00
(52) U.S. Cl. ..... Plt./118
(58) Field of Search ..... Plt./118, 125

*Primary Examiner*—Anne Marie Grunberg
*Assistant Examiner*—June Hwu

(57) ABSTRACT

A new miniature rose which has abundant, yellow and cream blend flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULhi018'.

SUMMARY OF THE INVENTION

The present invention constitutes a new and distinct variety of miniature rose plant which originated from a controlled crossing between the female parent, an un-named plant, and the male parent 'KORstoffein' described and illustrated in U.S. Plant Pat. No. 11,242, issued on Feb. 22, 2000. The two parents were crossed and the resulting seeds were planted in a controlled environment. The new variety is named 'POULhi018'.

The new rose may be distinguished from its seed parent, an un-named plant created by the same inventors, by the following combination of characteristics:

1. The seed parent has flower buds which are 28 mm in length from the base of the receptacle to the end of the bud, while 'POULhi018' is 19 mm.
2. The seed parent has a general tonality of Red-Purple Group 62D to Red Group 36D while 'POULhi018' is Yellow Group 2D with intonations of Yellow Group 12C.

The new variety may be distinguished from its pollen parent, 'KORstoffein', by the following combination of characteristics:

1. The average height of the pollen parent 'KORstoffein' is 60 cm while 'POULhi018' is more compact, with an average height of 17 to 20 cm.
2. The pollen parent 'KORstoffein' has a petal count of 25 to 30 while 'POULhi018' exhibits 50 petals under normal glasshouse conditions.
3. Upper surface of the outer petals of the pollen parent 'KORstoffein' are Yellow-Orange group 19D while the same of 'POULhi018' are Yellow Group 2D.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;

4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULhi018' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhi018' was selected by the inventors as a single plant from the progeny of the hybridization in the spring of 2001.

Asexual reproduction of 'POULhi018' by cuttings and traditional budding was first done by L. Pernille and Mogens N. Olesen in their nursery in Fredensborg, Denmark in July of 2001. This initial and other subsequent propagations conducted in controlled environments have demonstrated that the characteristics of 'POULhi018' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULhi018'. Specifically illustrated in FIG. 1:

FIG. 1.1; Open flower viewed from above, and open flower, side view with peduncle;

FIG. 1.2; Flower bud, partially opened bud, and open bloom;

FIG. 1.3; Sepals, receptacle, and pedicel;

FIG. 1.4; Flower petals, detached;

FIG. 1.5; Juvenile leaves and stem;

FIG. 1.6; Mature leaves;

FIG. 1.7; Bare stem.

DETAILED DESCRIPTION OF THE VARIETY

The following is a description of 'POULhi018', as observed in its growth in a glasshouses in Burlington, Canada. Plants are 10 weeks of age. Color references are made using The Royal Horticultural Society (London, England) Colour Chart, 1995, except where common terms of color are used.

For a comparison, several physical characteristics of the rose variety 'POULhi009', a rose variety from the same inventors described and illustrated in U.S. Plant patent application Ser. No. 10/267,976, dated Oct. 8, 2002, are compared to 'POULhi018' in Chart 1.

CHART 1

| | 'POULhi018' | 'POULhi009' |
|---|---|---|
| Petal Count | 50. | 40 to 45. |
| Basal Petal Spots | Yellow Group 2D to 6C. | Yellow Group 4A. |
| Outer Petal Color, Upper Side | Yellow Group 2D. | Yellow Group 4D. |
| General Tonality | Yellow Group 2D with intonations of Yellow Group 12C. | Yellow Group 6A. |

FLOWER AND FLOWER BUD

Blooming habit: Continuous.

Flower bud:

*Size.*—Upon opening, 19 mm in length from base of receptacle to end of bud. Flower buds are 11 mm wide.

*Bud form.*—Broad based pointed ovoid.

*Bud color.*—As sepals unfold, Yellow Group 4C; Yellow Group 4C at ¼ opening.

*Sepals.*—Upper Surface: Color: Yellow-Green Group 146A to Green Group 137A at the upper surface. Texture: Smooth. Lower Surface: Color: Yellow Green Group 146C with intonations of anthocyanin the color of Greyed-Purple Group 183C. Texture: Smooth with few stipitate glands along the margins. Shape: Sepal apex is cirrhose. Base is flat at union with receptacle. Margins have strong foliaceous appendages on three of the five sepals. Size: 40 mm long×7 mm wide.

*Receptacle.*—Surface: Smooth and lightly pubescent. Shape: Funnel. Size: 5 mm (h)×6 mm (w). Color: Green Group 144B.

*Peduncle.*—Surface: Smooth with few stipitate glands and light pubescensce. Length: 60 to 80 mm average length. Color: Green Group 144B. Strength: Upright, strong.

*Borne.*—Singly.

Flower bloom:

*Fragrance.*—Moderate rose scent.

*Duration.*—As a pot plant, flowers last from 15 to 18 days.

*Size.*—For a 15 cm pot rose, average flower diameter is 45 mm when open. Average flower depth is 19 mm.

*Form.*—Rosette. Shape of flower when viewed from the side: Upon opening, upper part: Flat. Upon opening, lower part: Flattened convex. Open flower, upper part: Flattened convex. Open flower, lower part: Flat.

*Petalage.*—Average range: 50 petals under normal conditions with 5 to 10 petaloids.

Color:

*Upon opening, petals.*—Outermost Petals Outer Side: Yellow Group 2D. Inner Side: Yellow Group 2D. Innermost Petals Outer Side: Yellow Group 2D. Inner Side: Yellow Group 2D.

*Upon opening, basal petal spots.*—Outermost Petals Outer Side: Yellow Group 2B. Inner Side: Yellow Group 2B. Innermost Petals Outer Side: Yellow Group 2B. Inner Side: Yellow Group 2B.

*After opening, petals.*—Outermost Petals Outer Side: Yellow Group 2D. Inner Side: Yellow Group 2D. Innermost Petals Outer Side: Yellow Group 2D to 6C. Inner Side: Yellow Group 2D to 6C.

*After opening, basal petal spots.*—Outermost Petals Outer Side: Yellow Group 2D to 6C. Inner Side: Yellow Group 2D to 6C. Innermost Petals Outer Side: Yellow Group 2D to 6C. Inner Side: Yellow Group 2D to 6C.

General Tonality: On open flower is Yellow Group 2D with intonations of Yellow 12C. No change in the general tonality at the end of the 10th day.

Petals:

*Petal reflex.*—Somewhat strongly.

*Petal edge.*—Entire with weak undulations of margin.

*Shape.*—Base shape is Acute to rounded. Apex shape is round with a slight point in the center of the margin.

*Size.*—21 mm in length by 19 mm wide.

*Thickness.*—Above average thickness.

*Surface texture.*—Smooth.

*Arrangement.*—Not formal.

Petaloids:

*Quantity.*—5 to 10.

*Size.*—8 mm long; 4 mm wide.

*Shape.*—Elliptic.

*Color.*—Yellow Group 2D to 6C on upper and lower surface.

Reproductive organs:

*Pollen.*—None Observed. Reproductive parts are incomplete.

*Anthers.*—None Observed. Reproductive parts are incomplete. Quantity:

*Filaments.*—None Observed. Reproductive parts are incomplete.

*Stigmas.*—None Observed. Reproductive parts are incomplete.

*Styles.*—Color: Yellow Green Group 145C, with intonations of Red-Purple Group 58B. Length: 8 mm.

*Seed formation.*—Not observed.

PLANT

Plant growth: Vigorous, compact, upright to bushy. When grown as a 15 cm pot plant, the average height of the plant itself is 17 cm and the average width is 15 cm.

Stems:

*Color.*—Young wood: Yellow Green Group 146A to 146B. Older wood: Yellow Green Group 146A to 146B.

*Length.*—15 cm.

*Diameter.*—3 mm.

*Surface texture.*—Young wood: Smooth. Older wood: Smooth.

Prickles: Incidence: None Observed.

Plant foliage: Normal number of leaflets on normal leaves in middle of the stem: 5 leaflets.

*Compound leaf size.*—95 mm (l)×65 mm (w).

*Color.*—Mature Foliage: Upper Leaf Surface: Green Group 137A to Yellow Green Group 146A. Lower Leaf Surface: Green Group 138B to 138C. Juvenile Foliage: Upper Leaf Surface: Yellow Green Group 144C. Lower Leaf Surface: Yellow Green Group 144C. Anthocyanin intonation: On plants grown under high light conditions, leaf margins and undersides of on developing leaves may exhibit intonations of Greyed-Purple Group 184A.

Plant leaves and leaflets:

*Stipules.*—Size: 8 mm in length. Shape: Linear with outward extending apecies. Color: Yellow Green Group 144A. Presence of stipitate glands: Margins.

*Petiole.*—Size: 15 mm long by 1 mm wide. Color: Yellow Green Group 144C. Underneath: Few prickles and stipitate glands observed.

*Rachis.*—Color: Yellow Green Group 144C. Underneath: Few prickles and stipitate glands observed. Margins: Stipitate glands observed.

*Leaflet.*—Size: 45 mm in length by 29 mm wide. Edge: Serrated. Overall Shape: Ovate. Apex Shape: Cuspidate. Base Shape: Round. Texture: Smooth. Thickness: Medium. Arrangement: Odd pinnate. Venation: Reticulate. Leaf Gloss: Matte appearance. Vein Color: Yellow Green 145A.

Disease resistance: Average resistance to mildew, black spot, and Botrytis under normal growing conditions in Burlington, Canada, and Fredensborg, Denmark.

What is claimed is:

1. A new and distinct variety of rose plant of the miniature class, substantially as herein illustrated and described as a distinct and novel rose variety due to its abundant, yellow and cream blend flowers, vigorous growth, compact habit, suitability for production from softwood cuttings in pots, and durable flowers and foliage which make the variety suitable for distribution in the floral industry.

* * * * *

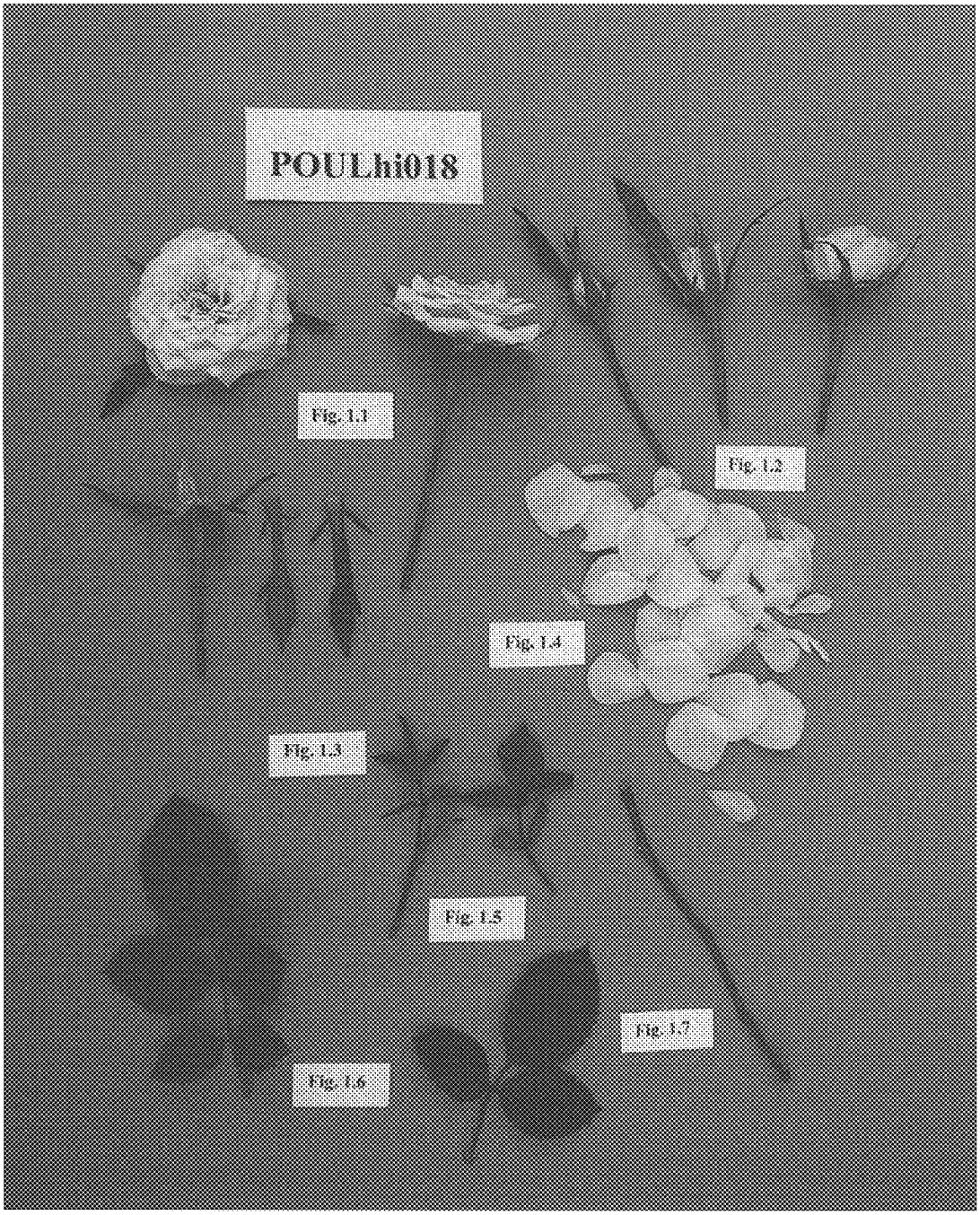
POULhi018
Fig. 1.1
Fig. 1.2
Fig. 1.4
Fig. 1.3
Fig. 1.5
Fig. 1.7
Fig. 1.6